United States Patent [19]

Sepponen

[11] Patent Number: 4,641,659
[45] Date of Patent: Feb. 10, 1987

[54] MEDICAL DIAGNOSTIC MICROWAVE SCANNING APPARATUS

[76] Inventor: Raimo E. Sepponen, Pitkansillanranta 7-9 C 111, 00530 Helsinki 53, Finland

[21] Appl. No.: 369,804

[22] Filed: Apr. 19, 1982

Related U.S. Application Data

[63] Continuation-in-part of Ser. No. 154,593, May 29, 1980, abandoned.

[30] Foreign Application Priority Data

Jun. 1, 1979 [FI] Finland .................................. 791771

[51] Int. Cl.$^4$ .............................................. A61B 5/05
[52] U.S. Cl. .................................................. 128/653
[58] Field of Search ....................... 128/653, 736, 804; 324/58.5 R

[56] References Cited

U.S. PATENT DOCUMENTS

| | | | |
|---|---|---|---|
| 2,814,298 | 11/1957 | Argento | 128/804 |
| 3,144,601 | 8/1964 | Slabodsky | 324/58.5 B |
| 3,278,841 | 10/1966 | Hanson et al. | 324/58.5 B |
| 3,483,860 | 12/1969 | Nomerow | 128/653 |
| 3,562,642 | 2/1971 | Hochschild | 324/58.5 R |
| 3,951,134 | 4/1976 | Malech | 128/653 |
| 4,135,131 | 1/1979 | Larsen et al. | 128/653 |
| 4,162,500 | 7/1979 | Jacobi et al. | 128/653 |

FOREIGN PATENT DOCUMENTS 862646 3/1961 United Kingdom ................ 128/804

OTHER PUBLICATIONS

Mallard, Jr. R. et al., "Dielectric Absorption of Microwaves in Human Tissues", *Nature*, vol. 213, No. 5071, Jan. 7, 1967, pp. 28-30.

Lehmann, J. F. et al., "Evaluation of a Microwave Contact Applicator", Archives of Phys. Med. & Rehabilitation, Mar. 1970, pp. 113-114.

*Primary Examiner*—Kyle L. Howell
*Assistant Examiner*—Francis J. Jaworski
*Attorney, Agent, or Firm*—Andrus, Sceales, Starke & Sawall

[57] ABSTRACT

Microwave apparatus for diagnosis of cancer of the breast includes a microwave transmitter and a microwave antenna for directing a microwave signal to the breast under examination, and a microwave receiver having amplitude and phase shift detectors for receiving of reflected microwave signals. A processor is connected to the receiver for processing the amplitude and phase information to detect and locate cancer in the breast. A matching plate having a dielectric constant substantially the same as normal breast tissue is located between and in engagement with the breast and antenna. The antenna engages and sweeps over the plane surface of the matching plate to eliminate any air gap in the transmission path. A display unit is connected to the processor to create a microwave image of cancer growth, if any.

5 Claims, 3 Drawing Figures

MEDICAL DIAGNOSTIC MICROWAVE SCANNING APPARATUS

This application is a continuation-in-part of application Ser. No. 154,593 filed May 29, 1980, and now abandoned.

BACKGROUND OF THE PRESENT INVENTION

This invention relates to apparatus for diagnosing pathological disorders such as cancer of the breast.

About 7% of women contract cancer of the breast. Of the cases nowadays detected, 50% lead to the patient's death within ten years of establishment of cancer. The prognosis is decisively dependent on how early the diagnosis can be made.

For diagnosing cancer of the breast are employed: X-ray examination, thermography, and manual palpation. Most efficient among these is X-ray examination, but owing to the high depth of penetration of X-rays in soft tissue, diagnosis of cancer in its initial stage is difficult by X-rays. A further detriment of X-rays is the radiation dose received by the patient, whereby X-ray examination is hardly applicable in mass screening.

Thermography is based on recording the infrared radiation emitted by the human body. This procedure is completely free of risk to the patient, but its reliability is poor (only 50% of cases diagnosed with X-ray apparatus are detected). Thermography is therefore only appropriate as a procedure supplementing X-ray examinations. The unreliability of thermography is due to the fact that it records only changes in the surface temperature of the skin, and such changes ensue as a consequence of cancer only when the neoplasm is large or located quite close to the skin surface.

Making a successful diagnosis by manual palpation implies that the neoplasm has already sufficient size, and it requires a certain experience on the side of the person making the diagnosis.

Also appearing on the scene nowadays are ultrasonic examinations, which are completely risk-free to the patient but are capable of diagnosis only if the neoplastic tissue is clearly encapsulated (that is, acoustically clearly differing from other tissues).

Summarizing the above, the observation may be made that nowadays no reliable procedure or apparatus is available which would be proper for earliest possible diagnosis of cancer of the breast, for instance with the aid of mass screening studies.

In the developing of the apparatus, that information served as starting point: that the breast tissue is comparatively homogeneous tissue resembling fat tissue, while cancerous tissue resembles muscle tissue in its electrical properties. On the basis hereof, microwaves are used for diagnosis in the apparatus of the invention.

In the following table (I) are presented the characteristics of tissues at the frequency of 10 GHz.

TABLE I

| | Wavelength, cm | Conductivity s | Dielectric constant Er | Depth of penetration, cm |
|---|---|---|---|---|
| Fat tissue | 1.4 | 0.3–0.5 | 4.5 | 3.4 |
| Muscle tissue | 0.5 | 10 | 40 | 0.5 |

In the following table (Table II) are given the coefficients of reflection of the tissue interfaces at frequency 10 GHz.

TABLE II

| | r (Coefficient of reflection) | $\phi$ (Phase Shift) |
|---|---|---|
| Fat/muscle interface | 0.5 | +175 |
| Muscle/fat interface | 0.5 | −6 |

As can be estimated from the values in the table, about 65% of the microwave radiation at 10 GHz frequency striking the cancerous tissue is reflected. As Table II reveals, reflection of microwaves takes place in the front and rear parts of the cancer growth, and each such reflection is also accompanied by a phase shift, of which the magnitude at different interfaces can be read in the table.

It is obvious on this basis that since the cancerous tissue is clearly different from normal breast tissue in its electric properties, microwaves can be used in diagnostics of cancer of the breast.

On the other hand, microwaves have been used in materials testing in various fields of industry. For instance, microwaves are used as aid in examinations of various coating layers for their thickness, materials for variations of porosity, for internal cracks, boards for knottiness, etc. But these types of apparatus of prior art are of such design that the idea of possibly constructing an apparatus, based on microwaves, for diagnosis of cancer of the breast is not at all suggested or obvious on their basis.

SUMMARY OF THE INVENTION

The apparatus of the invention for diagnosing cancer of the breast comprises, as components previously known in themselves, a microwave transmitter, a microwave wave antenna for the purpose of directing a microwave signal to the object under examination, a microwave receiver with amplitude and phase shift detectors, and a processor for processing the amplitude and phase information.

In order that these components known in prior art could be used in the apparatus of the invention for diagnosis of cancer of the breast and other pathological disorders and that the object of the invention, mentioned before, might be achieved, the apparatus is according to the teachings of the invention characterized in that the antenna has been arranged with the aid of a scanning mechanism to sweep over the surface of a matching plate, the breast under examination being pressable against the other side of this plate. The plate serves the purpose of matching the moving antenna with the tissue under examination, whereby the scanning mechanism may be comparatively simple because it has always to sweep over a plane. In order for the plate to accomplish this task in the best possible manner, the plate should have a dielectric constant substantially the same (Er about 5) as normal breast tissue.

It is possible with the apparatus of the invention to arrange for a microwave image consistent with the antenna scanning to be formed on a display.

BRIEF DESCRIPTION OF THE DRAWINGS

The following invention shall be illustrated by reference to the attached drawing wherein.

DESCRIPTION OF THE ILLUSTRATED EMBODIMENT

Figure 1:
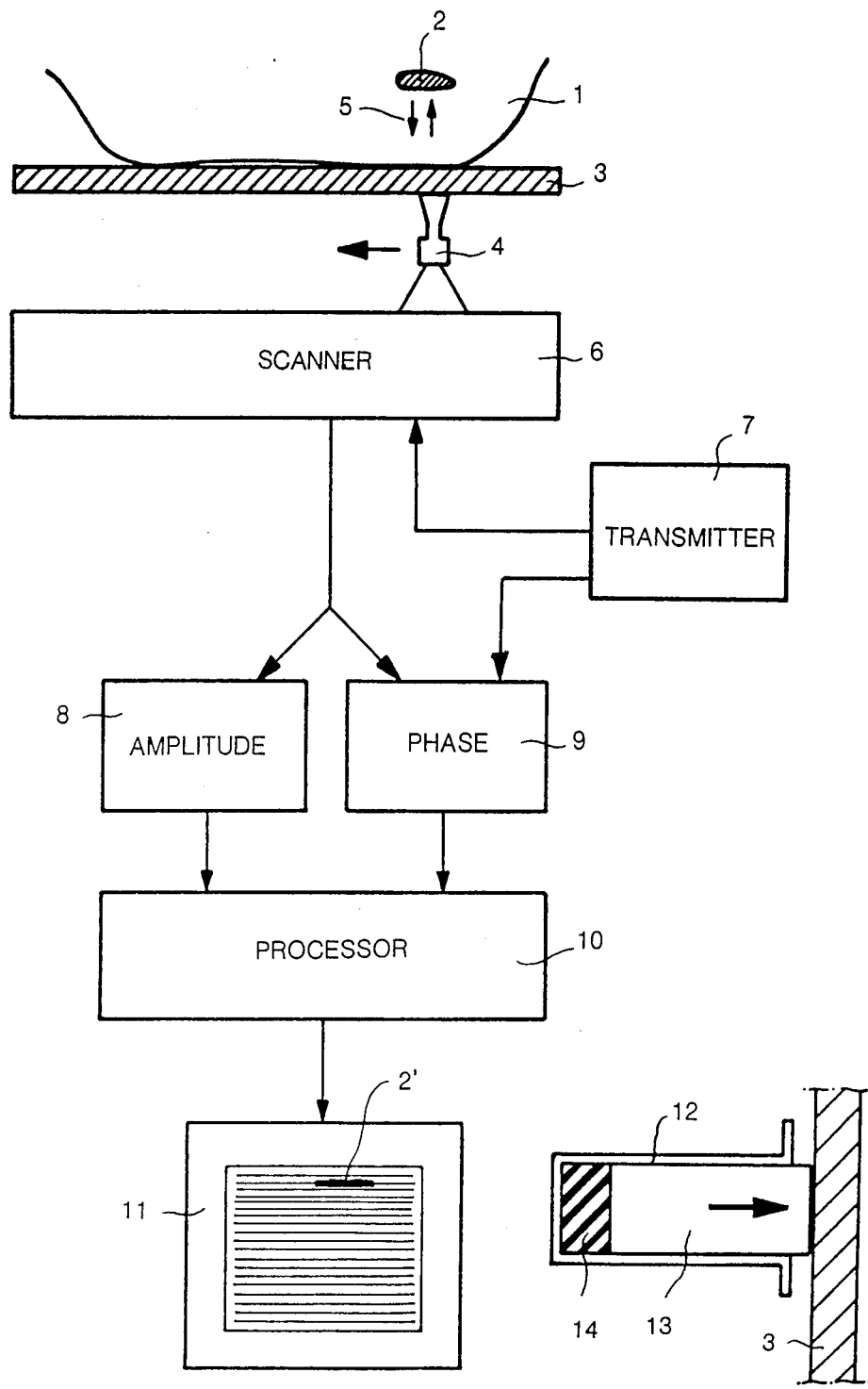
FIG. 1 is a diagrammatic illustration of a microwave scanner for diagnosing cancer of the breast and includes a signal processing system shown in block diagram.

As is well known, the shape, size and other characteristics of breast vary extensively. Since in microwave image forming it must be possible to match the transmitter and receiver with the skin and the subcutaneous fat with a view to avoiding unnecessary reflections, there has been provided, in the apparatus, a matching plate 3, which has been made of a material having a dielectric constant Er equal to the average dielectric constant of breast tissue (about 5). The breast to be examined, 1, is pressed against this matching plate 3. On the underside of the plate 3, the area to be examined is scanned with the microwave antenna system 4, governed by the scanning mechanism 6. The apparatus comprises, furthermore, a microwave transmitter 7 and a microwave receiver, with amplitude detector 8 and phase difference detector 9. The amplitude and phase information obtained from these is conveyed to the processor 10, which forms of the object under examination a microwave image, which is displayed with the display unit 11. In the case that there is a neoplasm 2, a conforming shadow 2' will be seen in the image in the display unit.

The contribution of the plate 3 to the image-forming is highly important: its effects matching of the moving antenna 4 with the tissue 1 under examination, and the scanning mechanism may be kept rather simple because the configuration to be scanned is always a plane. Moreover, the act of pressing the breast against the plate reduces the amount of venous blood during the image-forming process in the area under examination, thereby improving the sensitivity of diagnosis.

Figure 2:
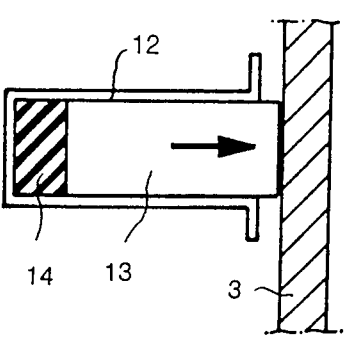
FIG. 2 illustrates a preferred mechanical design of an antenna unit.

The mechanical design of an advantageous embodiment of the antenna 4 is described in the following with reference being made to FIG. 2. As scanning antenna is used a wave guide 12 open at one end and filled e.g. with the material 13 used in the matching plate. Material 13 may be a piece of the plate. The problem is then: to maintain the end of the wave guide in continuous contact with the matching plate 3 so that during scanning between the antenna 4 and the plate 3 no air gap is produced, which would give rise to objectionable reflections. The matching plate 3 of the invention renders possible a simple solution of this problem: the matching material or piece 13 within the wave guide antenna is disposed to be movable in such manner that it is pressed out under spring action of an elastic material 14, or under gravity action if disposed in a vertical free moving through the open end of the wave guide 12, and the expressed end face of this matching material piece 13 follows along the surface of the matching plate 3. Continuous contact is hereby gained between the matching piece 13 and the matching place 3, and no air gaps giving rise to reflections can be formed.

Cancerous tissue is often encircled by a liquid layer that has been formed by the body's defensive mechanisms and which like muscular tissue reflects microwave radiation. This causes the cancerous growth to appear larger than actual size in the microwave image. This circumstance causes the requisite requirement of resolution to be less.

Regarding the power of resolution of the apparatus the observation can be made that it is able to identify among normal tissue those cancerous tissue particles which have a size more than one quarter of the wavelength employed, that is tissue particles about 4 mm in size when the frequency is 10 GHz. Of this, at least 1 mm is liquid surrounding the neoplasm, and therefore the size of the neoplasm is about 3 mm.

The frequency of 10 GHz employed in the apparatus is, technologically, fairly easy to control, and microwave components for operation within that wavelength range are available at a reasonable price. It is conceivable, with a view to improving the resolution, to increase the frequency if need by even up to 20 GHz.

Although the structure as shown in the drawings and described above will provide the basis for those skilled in the art to readily carry out the present invention for purposes of cancer or other physiological diagnosis, the various practical design considerations which will be applied by such personnel are briefly discussed to further minimize such routine activity requirement.

The system may use either a continuous wave mode of operation or a pulsed mode of operation. The selection of the desired mode will be determined by the availability of the source and the like and does not affect the validity of the results which will be obtained with the present invention. This is particularly true with the preferred construction as shown and described with respect to FIGS. 1 and 2. For example, in certain treatment apparatus in the prior art, heating of the body tissue requires special consideration. In the present invention, the matching plate 3 which provides the close coupling between the antenna and the body tissue produces interengagement or contact which significantly minimizes any probability of heating in the boundary surfaces or layers. Thus, whether a continuous or pulsed mode of operation is selected, the heating effect will be insignificant as long as the proper and ordinary care, such as normally required in any medical diagnostic instrument is taken. Similarly, the power level selected will vary with the particular other parameters which the design personnel selects, all of which are within the normal design criteria. Thus, the particular power level selected will be effected by such factors as the speed of scan, the sensitivity of the receiver, the deepness of the pathological area for growth or disorder to be imaged and diagnosed and the like. For example, the power level, for a continuous wave mode of operation is below the usual limit of ten microwatts per centimeter squares 10 mW/cm$^2$ over the usual operating frequency range. In a continuous mode of operation, a power level of 3 to 5 Mw/cm$^2$ would be typical of an optimum power range. The level should of course be sufficient to provide necessary imaging information. Further, although the frequency may vary widely, a frequency most appropriate for diagnostic purposes will be selected in the range of 0.5 to 10 gigahertz (GHz) with 0.5 to 5 GHz preferred.

Because the present invention minimizes and essentially avoids heating of any characteristic, the coupling plate is preferably a solid plate member such as described above and shown in the drawings. There is no need to provide any forced cooling of the plate such as by the circulation of a coolant dielectric through the plate. This is significant in connection with the described embodiment of invention because the solid plate does not include disturbing interfaces and avoids the possibility of reflection and disturbance of the transmitted and received wave signals. This of course is particularly significant in connection with a scanning mechanism where the characteristic of the matching plate is not maintained essentially constant over the total area to be scanned may introduce error into the total analysis because of variations from one area or point to the next. Once again the plate may be formed of any suitable dielectric material which can readily be provided by those skilled in the art. A particularly suitable material for the scanning plate is a "STYCAST epoxy 2850/GT" which is manufactured and sold by Emerson and Cumings Inc. of Canton, Mass. Such material has a dielectric constant (Er is essentially 5) which is essentially the same as that of the breast tissue. A close correlation between the dielectric constant of the plate and the breast tissue is important because disturbance of the signal through the matching plate and the interface is related to the difference in the dielectric constant. An identical dielectric constant would have minimal disturbance, which will increase as the dielectric constant of the breast tissue. For practical purposes, it is desired that the dielectric constant of the plate will not vary significantly from that of the breast tissue. The material of the plate 3 is not otherwise critical. The plate of course should not have any adverse genetic properties and of course has a proper surface characteristic to permit the spring-loaded forced engagement of the transmitting element of piece, as well as transmit the signals without significant distortion.

Figure 3:
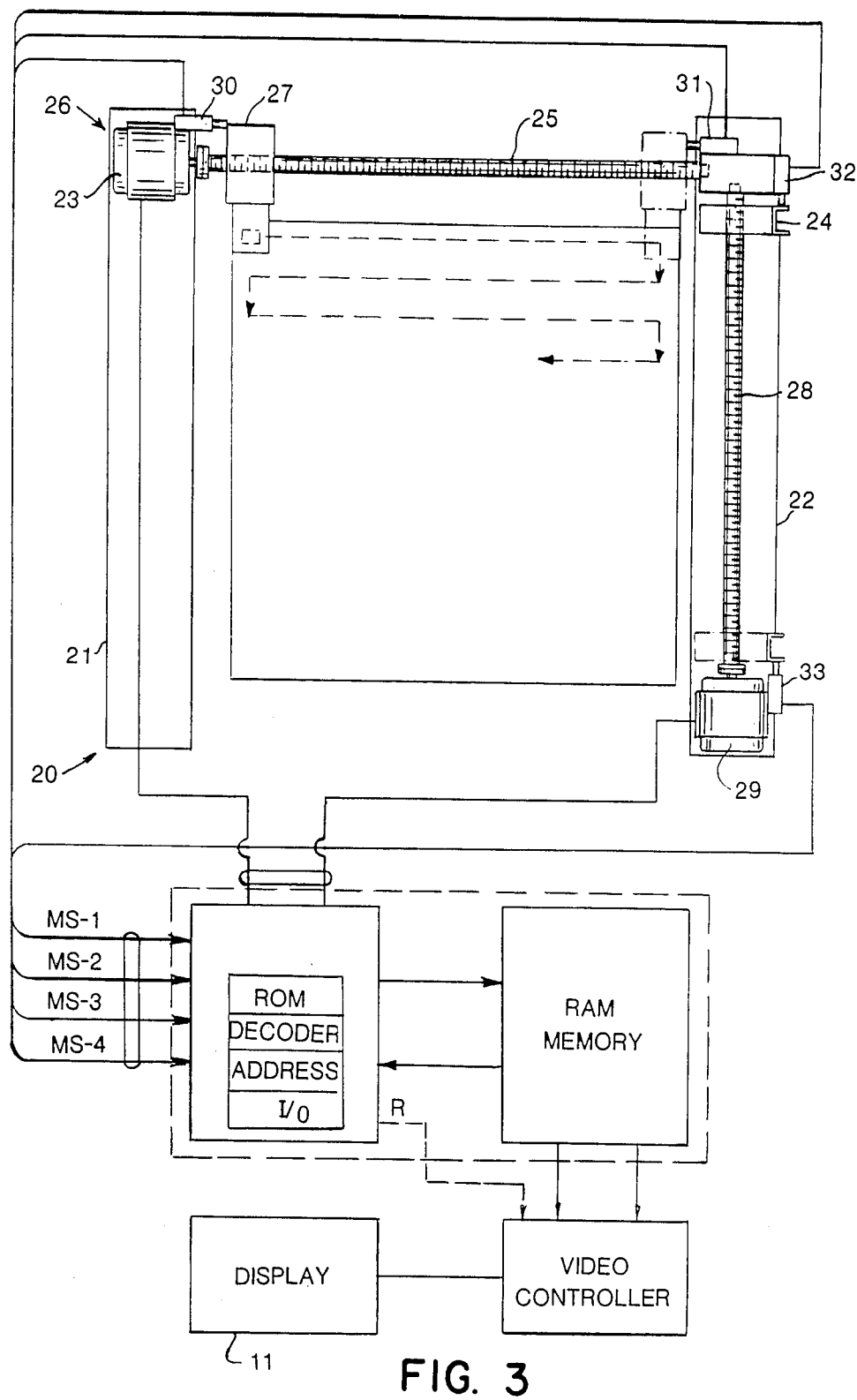
FIG. 3 illustrates a suitable positioning apparatus for the scanner shown in FIGS. 1 and 2.

Although any type of a scanning means might be employed, a simple, safe system is diagrammatically, illustrated in FIG. 3. In this embodiment of the invention, the transmitter/receiver assembly 6 and 7 includes a support structure 20 for movement over the dielectric plate 3. The support structure 20 is shown including tracks 21 and 22 located to the opposite sides of the dielectric plate 3. Carriage members 23 and 24 are mounted on the tracks for longitudinal movement along the tracks and over the dielectric plate 3. A lead screw 25 is rotatably mounted to the carriage members 23-24 and is coupled to a stepping motor 26 on the one carriage 23. The antenna 4 includes a follower 27 attached to the lead screw 25. The antenna 4 and the transmitter 6 and receiver 7 may be formed as a movable assembly mounted to the follower 27. Energization of the stepping motor 26 causes the antenna 4 to move across the dielectric plate 3. The stepping motor 23 is any suitable well known device adapted to provide timed movement of the antenna 4 across the dielectric plate 3. The carriage member 24 on the second track 22 is in turn mounted by a follower 24a on the second lead screw 28 extending perpendicular to the first for moving the lead screw 25 across dielectric plate 3. A second stepping motor 29 is mounted on the second track 22 and coupled to drive the lead screw 28 thereby causing the transport of the antenna across the dielectric plate 3, with a corresponding stepped movement of the assembly when energized.

In actual operation of course the antenna 4 is located to an initial starting position and then caused to traverse the dielectric plate 3. In the illustrated embodiment of the invention the first stepping motor 26 is operated to cause the antenna 4 to move across the dielectric plate 3 in a horizontal direction by a series of individual steps. At each step, a signal is generated providing corresponding image information. When antenna 4 reaches the opposite side of dielectric plate 3, the first stepping motor 26 is deenergized and the second stepping motor 29 is energized to move the antenna 4 along the length of the plate 3 one step. The stepping motor 26 is reversely operated to cause the opposite rotation of the lead screw 25 and a corresponding reverse scan movement of the antenna 4 to the left edge, as shown in FIG. 3. Upon the reaching of the left edge, the second stepping motor 29 is again energized to move the antenna 4 down another step. The above sequence of operation of the stepping motors 26 and 29 results in a traverse of the dielectric plate 3 as shown diagrammatically by line 29a (shown in expanded illustration), with data readings developed at each location to produce a sequence of individual bytes of information generated for each scanning of the dielectric plate. This, of course, provides a typical digital information matrix defining the image. The information may of course be suitably stored, processed and the like by any suitable means. With present technology, computer processor devices are readily available to control the stepping motors and to receive and process the data in well known manner.

For example, the limit positions of the antenna 4 may be monitored by four suitable microswitches 30, 31, 32 and 33 located, one each at the respective end limit positions of the antenna 4 on the lead screw 25 and lead screw 28, as shown in FIG. 3. Thus, switch 30 provides a signal indicating that the antenna 4 is in the initial start position and is conditioned to move to the right. When the assembly engages microswitch 31, a signal indicates that the antenna 4 has moved to the rightmost position and is to move downwardly one step and then return to the left. Microswitch 32 of course indicates the uppermost position for returning the antenna to the first line position. The microswitch 33 senses the final line position and defines a return signal which conjointly with the signal from the other switches causes the antenna 4 to return to its initial starting position.

The microswitches 30-33 thus provide all the information necessary to move the scanner. For example, the information can be supplied to a suitable computer which in turn provides appropriate signals to drive the motors 26 and 29. A typical computer system is shown in block diagram in FIGS. 1 and 3. As such systems are well known and will be readily understood by those skilled in the art, the computer is shown in simplified block diagram. The control may use any simple sequence programming system and can be readily provided by any one having basic skill in the art, a detailed description and program is therefore not given.

The processor of course includes a basic processor unit wherein suitable memories, decoders, addressing means, I/O means and the like are provided for manipulation of the analog data signals, conversion to digital format, appropriate processing and storage thereof in a RAM memory. The processor is programmed to continuously monitor the state of the microswitches 30-33 and thereby the position of the antenna 4 and to appropriately actuate the stepping motors 26 and 29. The processor 10 also receives and processes the image information. Such a system would basically include a RAM memory unit or section 35 within which a fixed program is provided for controlling the logical and sequential inputting of data, processing of such data, storing such data, and outputting such data. The RAM memory section 36 is provided for appropriate processing and storage of the data. The data is introduced and output through a suitable I/O unit connected to the external system by a common bus. The microprocessor of course operates in accordance with specific instructions which are contained within the control unit and the routing is controlled by appropriate addressing and decoding means, all under control from the basic program control unit. The operation and connection of the microprocessor will be readily understood by those skilled in the art, and the program listing of the reading, processing sequence and outputting of data based on the switch signals and data received and processed will be provided in a routine manner by those skilled in the art. This provides precise scanning of the dielectric plate 3 and therefore of the aligned patient's body. At each step, the processor actuates the transmitter/receiver assembly 6-7 to transmit a signal and record the reflected signal generated thereby. The signals are suitably processed by the processor 10 and stored directly in the RAM memory 36. The signals are typically analog signal generated by the transmitter/receiver assembly. Such analog signals as read are of course processed by a suitable digitizing unit for converting the signal into an appropriate form for processing and storage in a digital computer and particularly in the RAM memory. The location of the signal on the dielectric plate 3 and in the RAM memory 36 is of course interelated and provides the necessary matrixed information for subsequent processing and display.

The stored information can then of course be directly displayed through any suitable video display system in accordance with well known systems. Thus, shown in FIG. 3, a video controller unit 37 is coupled to the RAM memory 36 for reading of the memory locations in proper sequence and operates to drive the video display unit 11, reproducing the body image and thereby any physiological disorder which is detected by the last scan. The video controller 37 may of course be controlled by the processor 10 to maintain proper system operation for presentation and removal of information with respect to the RAM memory 36.

As such application of computer systems for capture and processing of signals is well developed art, no further detailed description thereof is deemed necessary or given herein.

In summary, during any diagnostic sequence, the processor 10 executes its program to actuate the stepping motors 26 and 29 in accordance with the sensed condition of the microswitches 30-33. This provides for a complete line-by-line scan of selected portion or the complete dielectric plate 3. The result of the scan of course is a corresponding matrix of image data words which are stored in the RAM memory, and which precisely defines the image. The image can therefore by reproduced on the video display unit or transmitted to other direct diagnostic analysis instrumentation, to a hard copy print-out system or the like. Of course any other control system may be used to properly move the antenna 4 and to receive the signals generated.

Various modes of carrying out the invention are contemplated as being within the scope of the following claims particularly pointing out and distinctly claiming the subject matter which is regarded as the invention.

I claim:

1. Apparatus for diagnosing cancer or other pathological disorder such as in the breast of a patient and having a microwave transmitting means (7) and a microwave antenna means (4) for directing a microwave signal to a breast under examination, cancer or other pathological disorder in said breast reflecting said microwave signal as a reflected microwave signal, a microwave receiving means having amplitude and phase difference detector means (8 and 9) for detecting said reflected microwave signals from the breast under examination and providing amplitude and phase information related thereto, a processing means connected to said receiving means (10) for processing said amplitude and phase information of said reflected microwave signal, display means (11) connected to said processing means for creating and displaying an image defined by said microwave signal, the improvement comprising a scanning mechanism (6) connected to move said antenna means (4) and thereby scan the breast under examination, and a matching plate (3) adapted to be interposed between the antenna means and the breast, said plate (3) having a dielectric constant substantially the same as that of normal breast tissue, said antenna means (4) being disposed on one side of said matching plate (3) to sweep over the surface thereof at least substantially in continuous contact and the breast (1) under examination being pressable against the other side of said plate (3).

2. Apparatus according to claim 1, wherein said antenna means (4) includes a wave guide (12) having an open end and an antenna member (13) located within the wave guide (12) and constructed and arranged to extend outwardly through said open end of said wave guide, and stressing means coupled to the antenna member and biasing said antenna member outwardly into close sliding engagement with said one side of said matching plate.

3. Apparatus according to claim 2, wherein said antenna member (13) is of the same material as said matching plate (3).

4. Apparatus for diagnosing pathological disorder of a patient and having a microwave transmitting means (7) and a microwave antenna means (4) for directing a microwave signal to the patient under examniation, receiver means for detecting signals from the patient under examination, the improvement comprising a scanning mechanism (6) connected to move said antenna means (4) and thereby scan the patient under examination, and a matching plate (3) adapted to be interposed between the antenna means and the patient, said plate (3) being a solid plate having a dielectric constant substantially the same as that of patient tissue, said antenna means (4) being disposed on one side of said matching plate (3) to sweep over the surface thereof at least substantially in continuous contact and the patient (1) under examination being pressable against the other side of said plate (3).

5. The apparatus of claim 4 where said receiver means includes amplitude detection means and phase difference detection means for detecting said reflected microwave signals and providing amplitude and phase signals as output related thereto, and a processing means is connected to said receiver means for recording and processing said signals.

* * * * *